United States Patent [19]

Fletcher et al.

[11] Patent Number: 5,609,581

[45] Date of Patent: Mar. 11, 1997

[54] SINGLE DOSE MEDICAMENT DISPENSER ASSEMBLY

[75] Inventors: Harry Fletcher, Bridgeton; Merrel J. Locke, Linwood, both of N.J.

[73] Assignee: Lawson Mardon Wheaton Inc., Millville, N.J.

[21] Appl. No.: 541,086

[22] Filed: Oct. 11, 1995

[51] Int. Cl.$^6$ .................................. A61M 5/178
[52] U.S. Cl. ............................ 604/212; 604/239
[58] Field of Search .................. 604/212, 207, 604/187, 216, 217, 239

[56] References Cited

U.S. PATENT DOCUMENTS 738,009  9/1903  Dews ........................... 604/212
3,354,883  11/1967  Southerland ................. 604/212 X

*Primary Examiner*—John D. Yasko
*Attorney, Agent, or Firm*—Eugene E. Renz, Jr.

[57] ABSTRACT

The combination comprising a container for a product having a puncturable diaphragm at one end thereof, an applicator of elongated parabolic shape including means for detachably mounting it on the container, an internal piercing element in the applicator aligned with the diaphragm and a plurality of discharge openings in the applicator, the applicator actuatable between an unarmed position wherein the piercing element is spaced from the diaphragm in an armed position where it punctures the diaphragm to permit discharge of the contents through the piercing element and the discharge openings in the applicator.

10 Claims, 4 Drawing Sheets

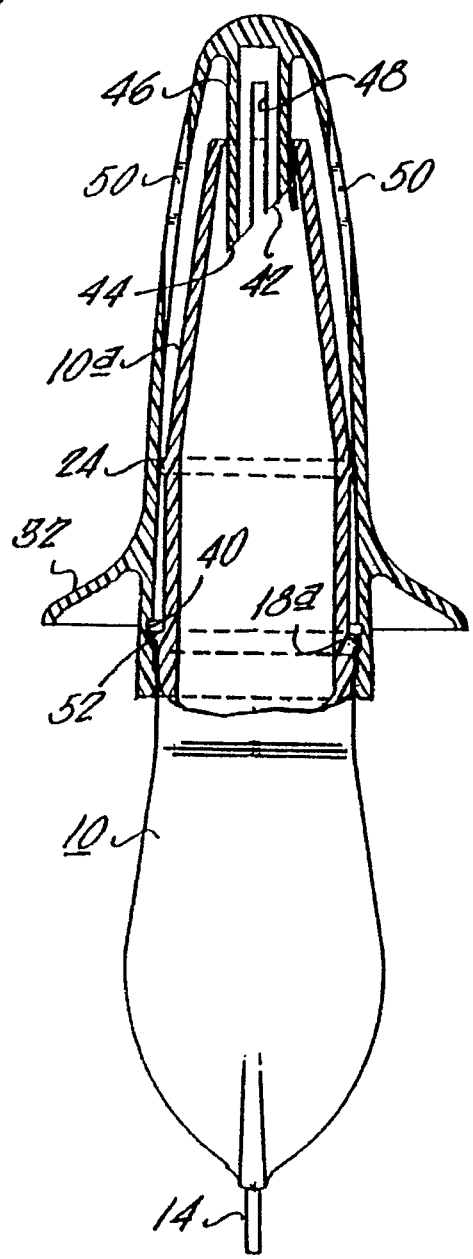
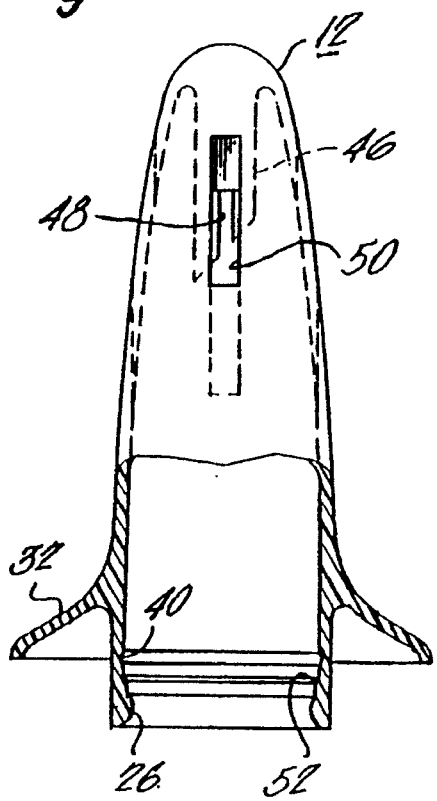
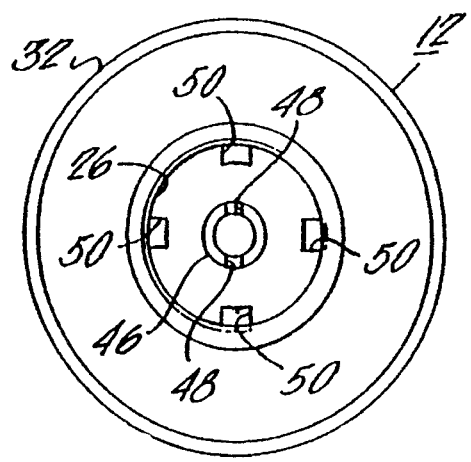

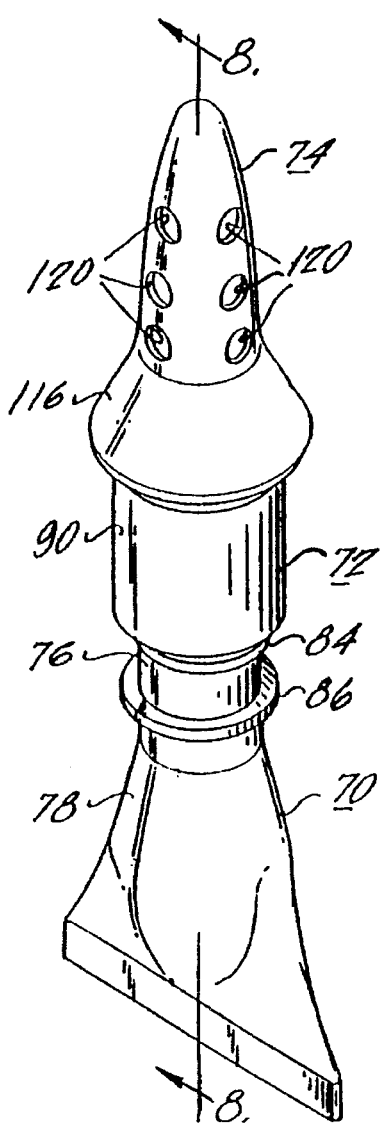
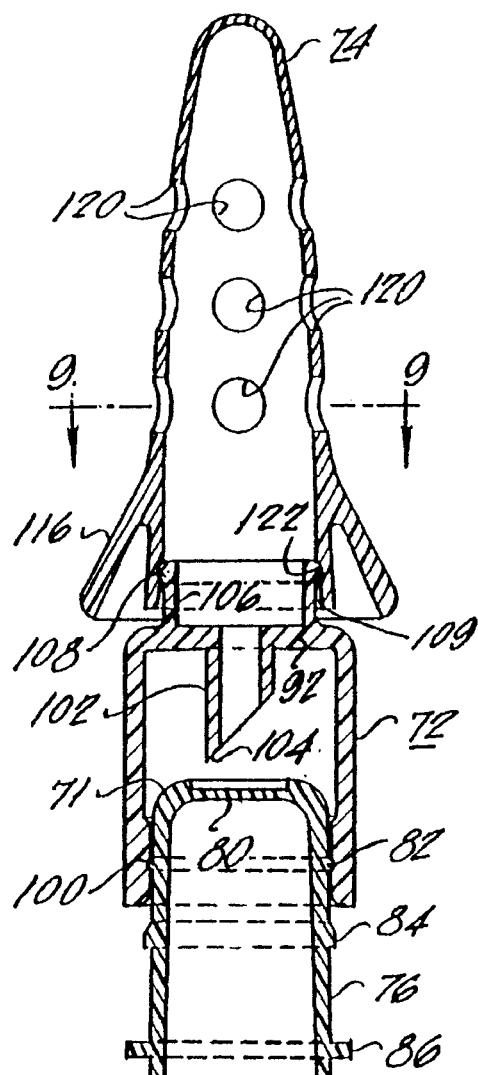
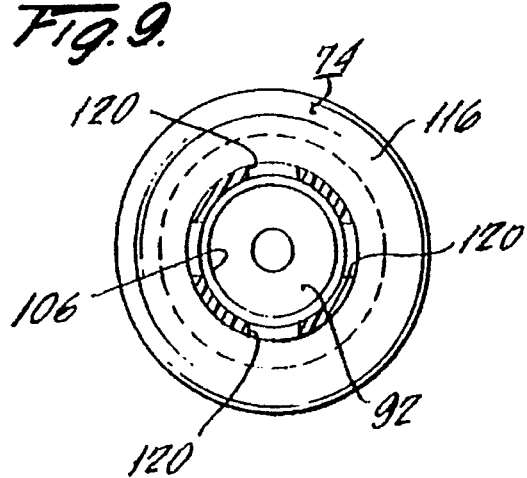

5,609,581

1

SINGLE DOSE MEDICAMENT DISPENSER ASSEMBLY

FIELD OF THE INVENTION

The present invention relates to medicament dispenser assemblies generally and more specifically to a new and improved disposable unit dose dispenser for pharmaceuticals injected rectally, such as pharmaceuticals used for the treatment of hemorrhoids.

BACKGROUND OF THE INVENTION

Packages presently used for dispensing pharmaceuticals used for the treatment of hemorrhoids, consist of a reusable tube with a separate applicator. This package assembly has certain disadvantages and drawbacks. For example, after each use, the applicator must be cleaned and stored in a place to protect the cleanliness of the applicator for the next use. An advantage of this system is the plural uses available from each tube.

In some instances, the package assembly consists of a tube containing plural dosages and a plurality of applicators, so that each time the robe is used, a new applicator is applied to end of the tube. However, this arrangement likewise has some draw backs. For example, a negative is that the user must assemble the applicator each time it is used and there is a reluctance on part of the user to throw away the used applicator, since it is still functional and use does not destroy it to a point of preventing re-use.

Accordingly, the desiderata is a unit of use tube that is so economical that it will compete with the multiple use tube and a package that is user friendly and will provide the individual protection that is needed and desirable.

SUMMARY OF THE INVENTION

With the above in mind, it is an object of the present invention to provide a unit of use packaging and dispenser assembly particularly adapted for use rectally for pharmaceuticals such as those used for the treatment of hemorrhoids.

The parts comprising the dispenser assembly are of relatively simple non-complex design and lend themselves to multiple cavity molding and automatic assembly. Accordingly, the cost of manufacturing and assembling these disposable single unit of use dispenser assemblies is quite reasonable.

BRIEF DESCRIPTION OF THE DRAWINGS

These and other objects of the present invention and the various features and details of the operation and construction thereof are hereinafter more fully set forth with reference to the accompanying drawings, wherein;

FIG. 4 is an enlarged side elevational view with a portion broken away and in section showing the dispenser assembly in an armed mode;

2

Figure 10:
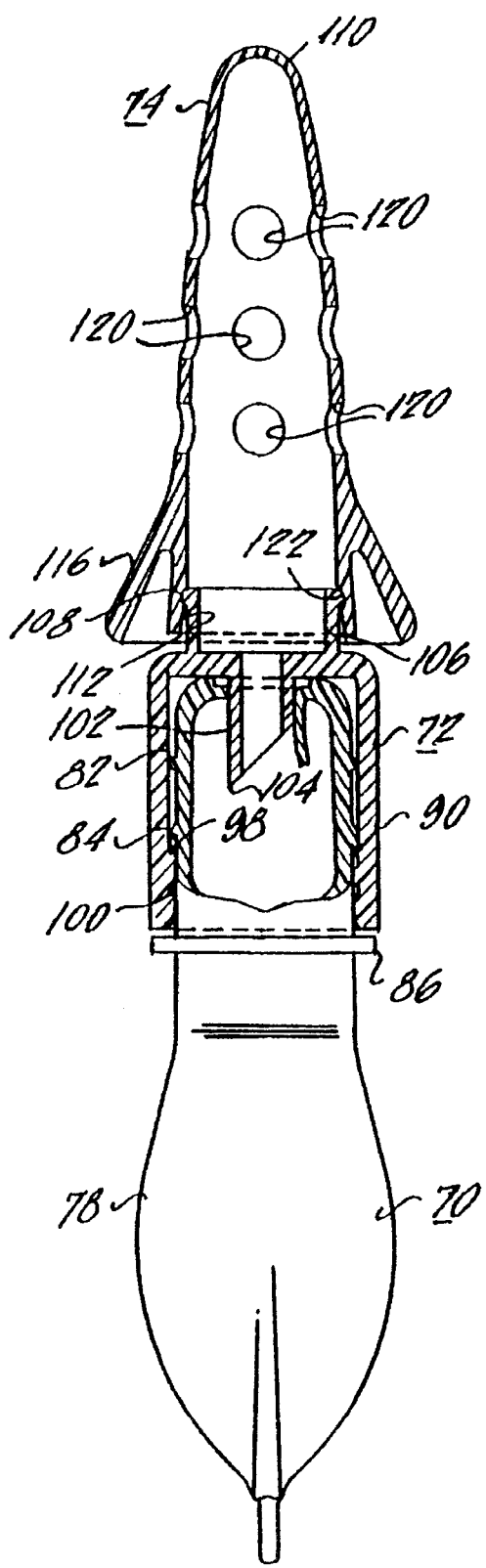
Figure 11:
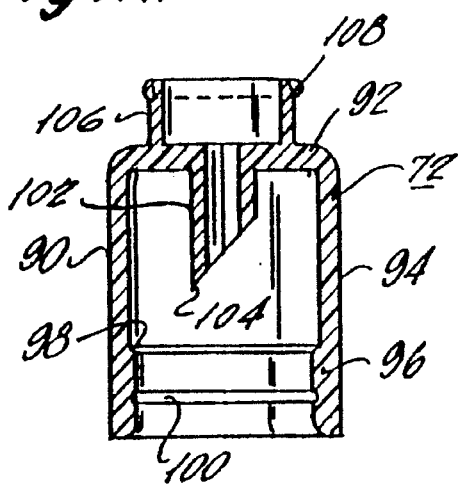

FIG. 5 is a side elevational view of the applicator part of the assembly with a portion broken away and in section showing the construction and configuration of the lower terminal end of the applicator;

FIG. 6 is a bottom plan view of the applicator shown in FIG. 5;

FIG. 7 is a enlarged isometric view of another embodiment of unit dose dispenser assembly in accordance with the present invention;

FIG. 8 is a greatly enlarged sectional elevational view taken on lines 8—8 of FIG. 7 showing the positions of the parts of the assembly in an unarmed mode;

FIG. 9 is a sectional plan view taken on lines 9—9 of FIG. 8;

FIG. 10 is an enlarged elevational view of the dispenser assembly with a portion broken away and in sections showing the parts of the assembly in an armed mode;

FIG. 11 is a sectional elevational view of the pierce point adapter; and

Figure 12:
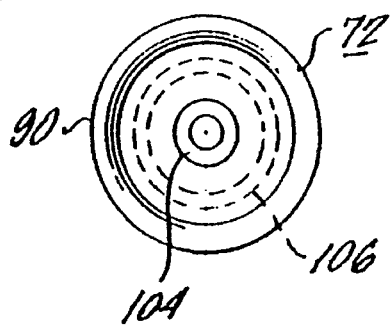

FIG. 12 is a bottom plan view of the adapter shown in FIG. 11.

DETAILED DESCRIPTION OF THE PREFERRED EMBODIMENT

Referring now to the drawings and particularly to FIGS. 1–6 thereof, there is shown an embodiment of anal dispenser assembly in accordance with the present invention broadly comprising a container or package (10) for the pharmaceutical product to be dispensed and an applicator (12). The package or container (10) and dispenser and applicator are preferably made of a plastic material, such as polypropylene.

The package (10) is of a size to hold a single dose of a pharmaceutical product, such as an ointment, and is initially of tubular form open at its lower end for filling purposes and after being filled, the lower edges are heat sealed as at (14). The cross-section of the tubular body portion is stepped at about its mid point as at (18) to define circumferentially extending beaded shoulder (18a) utilized in locking the applicator (12) to the package (10) in the use or armed position shown in FIG. 4 below. The upper portion of the tube is flared inwardly and of nozzle shape and terminates at its upper in a thin walled piercable diaphragm section (22). A circumferentially extending, radially outwardly directed bead (24) is provided on the exterior surface of the container at the juncture of the tapered top portion and the generally cylindrical transition portion (10a) and (10b) respectively for retaining the applicator (12) in an unarmed mode by means of a cooperating circumferentially extending groove (40) formed in the applicator body.

Figure 1:
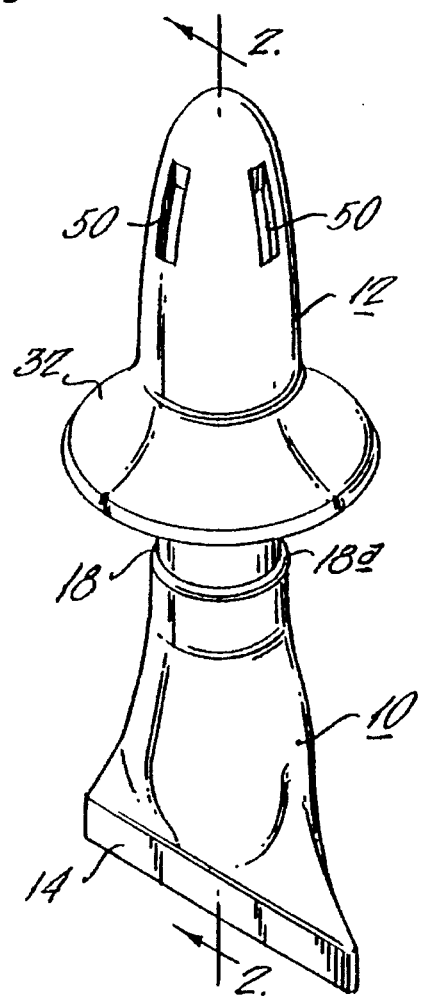
FIG. 1 is an enlarged isometric view of a unit dose anal dispenser assembly in accordance with the present invention.

The applicator (12) as best shown in FIGS. 1 and 5 is a thimble like element, generally cone shaped as shown having a arcuate nose of a size and shape for easy insertion in the rectal canal and opened at its inner end as at (26). The spaced upwardly from the inner open end of the applicator is an outwardly rearwardly flared flange (32), which is frusto conical in shape and extends at about a 45° angle from the generally tubular wall of the applicator in the manner shown in FIG. 5. This shield limits penetration of the applicator head into the rectal canal and insures proper positioning of the applicator for dispensing the pharmaceutical product in the container and provides a finger guard.

Figure 2:
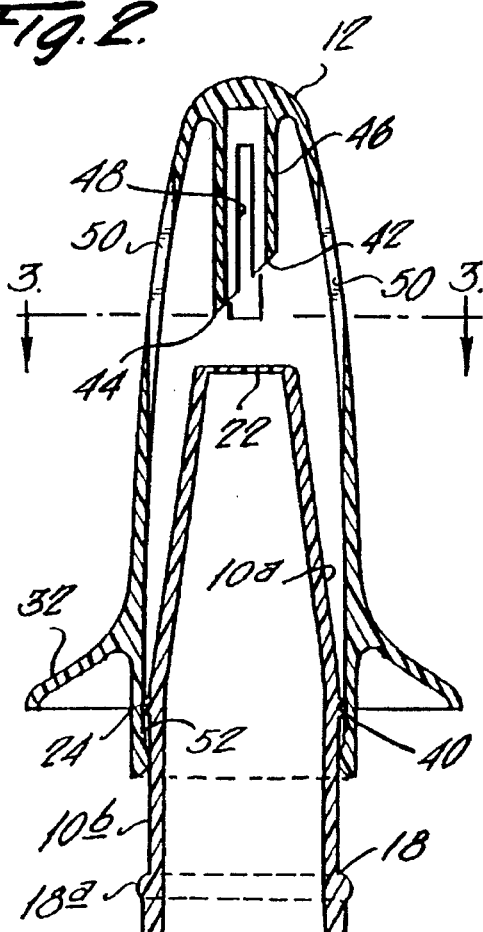
FIG. 2 is a greatly enlarged sectional elevational view taken on lines 2—2 of FIG. 1 showing the relative position with the parts comprising the dispenser in an unarmed mode.
Figure 3:
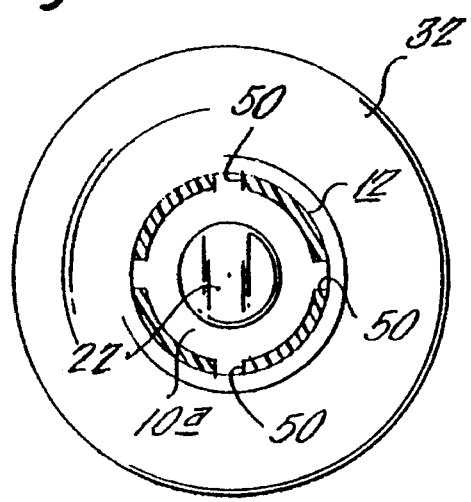
FIG. 3 is a sectional plan view taken on lines 3—3 of FIG. 2.

The inner peripheral surface of the body portion of the applicator is provided with a circumferentially extending groove (40) spaced upwardly from the lower terminal end, which cooperatively provides a seat for the bead (24) on the container (12) to position the applicator in the unarmed mode shown in FIG. 2 where the piercing element is spaced from the diaphragm.

A hollow piercing element (46) depends from the inner portion of the tip of the applicator and has a biased inner terminal edge as at (42) to define a piercing point (44) to puncture the diaphragm when the applicator is moved to an armed position shown in FIG. 4. The piercing element (46) is of generally cylindrical or tubular shape, a pair of diametrically opposed or slits (45) extend from its inner terminal end almost to the tip of the applicator as shown in FIG. 4. These slits provide a flow passage for the pharmaceutical product. The sidewall of the applicator is provided with discharge ports or passage ways (50). In the present instance, there are four elongated passage ways circumferentially equi spaced about the periphery of the applicator.

When in the armed or use position as shown in FIG. 4, it is important that the applicator (12) remains securely fixed to the dispenser body (12). To this end the lower terminal end (26) of the applicator (12) is provided with an internal inwardly directed circumferentially extending stepped shoulder (52), which in the armed position shown in FIG. 4 underlies the bead (102) on the package (10) effectively locking the applicator (12) to the package (10).

The dispenser-applicator assembly is of a design lending itself to low cost injection molding and to filling and sealing of the container by automatic assembly techniques. The applicator (15) positioned over the discharge end of the container in an unarmed position where the bead on the container engages in the internal groove in the applicator. Now when the user desires to dispense the pharmaceutical product in the container, the applicator is simply displaced axially downwardly whereby the piercing element punctures the diaphragm in the manner shown in FIG. 4. The applicator engages over the lower bead on the container in its lower most position, whereby a portion of the slots in the piercing element are disposed above the discharge end of the container to provide a flow passage for the pharmaceutical to discharge the container and pass through the openings in the sidewall of the applicator. The user simply inserts the applicator into the rectal opening until it bottoms gently on the flared flange and then presses the container to dispense the ointment. The entire device can then be discarded since it is a unit dose applicator of a relatively low cost.

There is shown in FIGS. 7–12 inclusive a modified form of dispenser-applicator assembly in accordance with the present invention. In accordance with this embodiment, the assembly comprises a container or tube (70), and adapter (72) and an applicator (74). The tube (70) has a generally cylindrical nozzle portion (76) and a flared body portion (78), open at its lower end to facilitate filling of the tube. After filling the lower end of the tube (70) is sealed by conventional pressure and heat sealing apparatus. The discharge end (71) of the tube has a puncturable diaphragm (80) of reduced cross section and a series of locking rings or ribs (82) and (84) on the outer peripheral surface to cooperate with the adapter (72) in various operative positions and a circumferentially extending flange (86) below the ribs (82) and (84), defining a stop for the adapter (72).

The adaptor (72) as best illustrated in FIGS. 11 and 12 is an elongated tubular member including a lower portion (90) of cap like form having a top (92) and a circumferentially extending depending skirt (94). The lower terminal end of the skirt (94) is of a increased wall thickness as at (96) to define a step or shoulder (98) which cooperates with one of the locking beads on the container to hold the adapter (72) in a armed position in the manner described in more detail below. A circumferentially extending groove (100) is provided on the inner peripheral surface of the enlarged skirt portion (96) which as illustrated in FIG. 8, engages over the top locking bead or rib (82) on the tube when the assembly is in the unarmed mode or position. A hollow piercing element (102) having a pointed piercing tip (104) which is hollow, depends from the top (92). The adapter has an upwardly projecting, circumferentially extending mounting boss (106) detachably supporting the applicator (74). Specifically, the mounting boss (106) has a bead (108) at its upper terminal end which snap fits in a groove (122) in the applicator (74) to support the applicator (74) in place in the manner shown in FIGS. 8 and 10. In practice it may be desirable to weld the applicator (74) to the adaptor (72) in the region of the bead and groove zone.

The applicator (74) is generally similar in overall configuration and arrangement to that described in connection with the principal embodiment and is a thimble like element, generally cone shaped member having an arcuate nose (110) of a size and shape for easy insertion in the rectal passageway and open at its lower end as at (112). Spaced upwardly from the open end of the applicator (74) is a downwardly flared flange (116) which is frusto conical in shape and extends at about a 30° angle to the central axis of the applicator (74). The flange (116) provides a shield limiting penetration of the applicator head into the rectal passageway and insures proper positioning of the applicator (74) for dispensing the pharmaceutical product in the tube. The side walls of the applicator are pierced by two series of three vertically spaced holes (120) positioned at 90° intervals about the periphery of the applicator nozzle. This is an important feature since the positioning of the holes insures the medication is dispensed against the side walls of the canal and not just into the canal. The inner surface of the body portion of the applicator (74) is provided with a circumferentially extending groove (122) spaced upwardly from the lower terminal edge, which provides a seat for supporting the applicator (74) on the bead (108) and support boss (106) of the adapter (72).

Consider now, use of a filled tube. In the filled tube, the parts are initially in the unarmed mode shown in FIG. 8. In this position, the applicator (74) is detachably supported on the adapter support sleeve in the manner shown. The inner edge surface of the applicator (74) is flared outwardly as at (109) for ease of assembly and mounting of the applicator (74) on the adapter boss. The applicator (74) is initially positioned so that the locking bead (82) is engaged in the groove (100) in the adapter and the piercing point of the piercing element is spaced above the diaphragm (80). Now, when the user desires to dispense product from the tube, the user simply applies a downward force through the applicator (74) which in turn displaces the adapter (72) downwardly. During downward movement, the piercing element punctures the diaphragm (80) to establish a fluid communication between the product and the applicator (74). It is noted that as the adapter (72) bottoms out, the locking rib (84) engages above the shoulder portion (98) of the adapter (72) to lock the adapter (72) and the applicator (74) in position and prevent it from being displaced upwardly during dispensing of the product. The user then simply positions the applicator (74) in place and squeezes the tube to dispense product.

Even though particular embodiments of the present invention have been illustrated and described herein, it is not intended to limit the invention and changes and modifications may be made therein within the scope of the following claims.

What is claimed is:

1. The combination comprising a container for a product having a puncturable diaphragm at one end thereof, an applicator of elongated parabolic shape including means for detachably mounting it on the container, an internal piercing element in the applicator aligned with said diaphragm and a plurality of discharge openings in the applicator, and a circumferentially extending outwardly and flexible rearwardly flared flange extending from the lower end of the applicator to limit penetration when inserting the applicator in a body opening, said applicator actuatable between an unarmed position wherein the piercing element is spaced from the diaphragm and an armed position where it punctures the diaphragm to permit discharge of the contents through the piercing element and the discharge openings in the applicator.

2. The combination comprising a container for a product having a puncturable diaphragm at one end thereof, an applicator of elongated parabolic shape including means for detachably mounting it on the container, an internal piercing element in the applicator aligned with said diaphragm and a plurality of discharge openings in the applicator, said applicator actuatable between an unarmed position wherein the piercing element is spaced from the diaphragm and an armed position where it punctures the diaphragm to permit discharge of the contents through the piercing element and the discharge openings in the applicator;

said piercing element being hollow and having at least one longitudinal slot and means limiting displacement of said applicator when arming same so that a portion of the slot extends above the diaphragm to establish a flow path through the piercing element in the armed position.

3. The combination as claimed in claim 2 wherein the applicator is generally cone shapes having an arcuate nose of a size and shape for easy insertion in a body opening and an outwardly rearwardly flared flange adjacent the open inner end of the applicator.

4. The combination as claimed in claim 3 wherein the flared flange is frusto conical in shape and extends at about a 45° angle from the axis of the applicator.

5. The combination as claimed in claim 2 wherein the applicator and container include interengaging detachable locking means for normally positioning the applicator in the unarmed position.

6. The combination as claimed in claim 5 where the interengaging locking means comprises a peripheral bead on the container which engages in a groove on the inner peripheral surface of the applicator.

7. The combination as claimed in claim 2 wherein the applicator engages over a top portion of the container and is slidable relative thereto and including a shoulder engageable by the lower terminal edge of the applicator to limit penetration of the piercing element and determine the armed position.

8. The combination comprising a container for a product having a puncturable diaphragm at one end thereof, an applicator of elongated parabolic shape including means for detachably mounting it on the container, an internal piercing element in the applicator aligned with said diaphragm and a plurality of discharge openings in the applicator, said applicator actuatable between an unarmed position wherein the piercing element is spaced from the diaphragm and an armed position where it punctures the diaphragm to permit discharge of the contents through the piercing element and the discharge openings in the applicator; and an adaptor positioned between the applicator and container carrying said piercing element.

9. The combination as claimed in claim 8 wherein the adapter comprises an elongated tubular member including a lower portion of cup like form having a top and a circumferentially extending depending skirt, the lower terminal edge of the skirt being of increased wall thickness to define a step or shoulder which cooperates with a locking bead on the container to locate the adapter in an armed position.

10. The combination as claimed in claim 9 including a circumferentially extending groove on the inner peripheral surface of the enlarged skirt portion which engages over a locking bead on the tube when the assembly is in the unarmed position.

* * * * *